US010478329B2

(12) United States Patent
Oberholtzer et al.

(10) Patent No.: US 10,478,329 B2
(45) Date of Patent: Nov. 19, 2019

(54) OSTOMY POUCH FILTER SYSTEM

(71) Applicant: ConvaTec Technologies Inc., Las Vegas, NV (US)

(72) Inventors: Gary Oberholtzer, Greensboro, NC (US); Marc Lesko, Jackson, NJ (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 377 days.

(21) Appl. No.: 15/306,043

(22) PCT Filed: Apr. 24, 2015

(86) PCT No.: PCT/US2015/027661
§ 371 (c)(1),
(2) Date: Oct. 21, 2016

(87) PCT Pub. No.: WO2015/164832
PCT Pub. Date: Oct. 29, 2015

(65) Prior Publication Data
US 2017/0042723 A1    Feb. 16, 2017

Related U.S. Application Data

(60) Provisional application No. 61/983,998, filed on Apr. 24, 2014.

(51) Int. Cl.
*A61F 5/441* (2006.01)
*A61F 5/445* (2006.01)

(52) U.S. Cl.
CPC .............. *A61F 5/441* (2013.01); *A61F 5/445* (2013.01)

(58) Field of Classification Search
CPC combination set(s) only.
See application file for complete search history.

(56) References Cited

U.S. PATENT DOCUMENTS

| 4,411,659 | A | * | 10/1983 | Jensen | ................... | A61F 5/441 |
| | | | | | | 604/332 |
| 4,826,495 | A | * | 5/1989 | Petersen | ................. | A61F 5/441 |
| | | | | | | 604/333 |
| 5,074,851 | A | * | 12/1991 | Plass | ...................... | A61F 5/441 |
| | | | | | | 604/333 |
| 5,167,650 | A | * | 12/1992 | Johnsen | ........... | A61B 17/32053 |
| | | | | | | 604/332 |
| 5,250,042 | A | * | 10/1993 | Torgalkar | ................ | A61F 5/441 |
| | | | | | | 604/333 |

(Continued)

FOREIGN PATENT DOCUMENTS

| EP | 0443728 A2 | 8/1991 |
| EP | 2621418 A1 | 8/2013 |

(Continued)

OTHER PUBLICATIONS

Australia Patent Application No. 2016266028 Examination Report No. 1 dated Sep. 12, 2017.

(Continued)

*Primary Examiner* — Tatyana Zalukaeva
*Assistant Examiner* — Guy K Townsend
(74) *Attorney, Agent, or Firm* — Wilson Sonsini Goodrich & Rosati

(57) ABSTRACT

Ostomy appliances with a filter system that is resistant to clogging by waste expelled by the stoma are provided for waste management.

29 Claims, 8 Drawing Sheets

(56) References Cited

U.S. PATENT DOCUMENTS

| | | | |
|---|---|---|---|
| 5,306,264 A * | 4/1994 | Ferguson | A61F 5/441 604/332 |
| 5,348,546 A * | 9/1994 | Norton | A61F 5/445 604/332 |
| 5,401,264 A | 3/1995 | Leise, Jr. | |
| 5,468,235 A * | 11/1995 | La Gro | A61F 5/441 604/333 |
| 5,643,234 A * | 7/1997 | Lesko | A61F 5/441 604/333 |
| 5,690,623 A | 11/1997 | Lenz et al. | |
| 6,328,719 B1 * | 12/2001 | Holtermann | A61F 5/441 604/332 |
| 6,712,800 B2 | 3/2004 | Kanbara | A61F 5/441 604/333 |
| 7,083,569 B2 | 8/2006 | Boulanger et al. | |
| 7,214,217 B2 | 5/2007 | Pedersen et al. | |
| 7,476,220 B2 | 1/2009 | Lillegaard | |
| 7,572,492 B2 | 8/2009 | Bager et al. | |
| 7,604,622 B2 | 10/2009 | Pedersen et al. | |
| 2003/0004476 A1 * | 1/2003 | Kanbara | A61F 5/441 604/333 |
| 2003/0014023 A1 * | 1/2003 | Kanbara | A61F 5/441 604/333 |
| 2003/0040727 A1 | 2/2003 | Boulanger et al. | |
| 2005/0075616 A1 * | 4/2005 | Holter | A61F 5/445 604/332 |
| 2005/0143696 A1 | 6/2005 | Pedersen et al. | |
| 2007/0027434 A1 * | 2/2007 | Pedersen | A61F 5/441 604/333 |
| 2007/0049880 A1 | 3/2007 | Suehr et al. | |
| 2007/0203466 A1 | 8/2007 | Pedersen et al. | |
| 2008/0004580 A1 | 1/2008 | Mullejans et al. | |
| 2008/0306459 A1 * | 12/2008 | Albrectsen | A61F 5/441 604/333 |
| 2009/0227973 A1 * | 9/2009 | Worsoee | A61F 5/441 604/333 |
| 2009/0247970 A1 | 10/2009 | Keleny et al. | |
| 2010/0241092 A1 | 9/2010 | Nguyen-Demary et al. | |
| 2012/0283678 A1 | 11/2012 | Nguyen-Demary et al. | |
| 2013/0085463 A1 * | 4/2013 | Lesko | A61F 5/441 604/333 |
| 2014/0194843 A1 * | 7/2014 | Masters | A61F 5/4405 604/333 |
| 2016/0278969 A1 * | 9/2016 | De Weert | A61F 5/441 |
| 2017/0042723 A1 * | 2/2017 | Oberholtzer | A61F 5/445 |

FOREIGN PATENT DOCUMENTS

| | | |
|---|---|---|
| EP | 3134040 A1 | 3/2017 |
| GB | 2149306 A | 6/1985 |
| GB | 2116433 B | 8/1985 |
| GB | 2461721 A | 1/2010 |
| JP | S6121414 B2 | 5/1986 |
| JP | 2003019154 A | 1/2003 |
| JP | 2005211178 A | 8/2005 |
| WO | WO-2012044910 A1 | 4/2012 |
| WO | WO-2015164832 A1 | 10/2015 |

OTHER PUBLICATIONS

Canadian Patent Application No. 2,813,248 Office Action dated Oct. 23, 2017.
European Patent Application No. 15783238.7 extended European Search Report dated Nov. 23, 2017.
Japanese Patent Application No. 2016-177009 Office Action dated Jul. 25, 2017.
U.S. Appl. No. 13/248,704 Office Action dated Jun. 1, 2017.
Chinese Patent Application No. 201180057593.X 4th Office Action dated Jun. 30, 2016.
European Patent Application No. EP11829957.7 Supplementary European Search Report completed May 14, 2014.
Japanese Patent Application No. 2013-531905 Decision of Rejection dated May 10, 2016.
PCT/US2011/054177 International Preliminary Report on Patentability dated Apr. 2, 2013.
PCT/US2011/054177 International Search Report and Written Opinion dated Jan. 23, 2012.
PCT/US2015/027661 International Search Report and Written Opinion dated Jul. 30, 2016.
U.S. Appl. No. 13/248,704 Office Action dated Aug. 13, 2014.
U.S. Appl. No. 13/248,704 Office Action dated Dec. 3, 2014.
U.S. Appl. No. 13/248,704 Office Action dated Feb. 27, 2014.
U.S. Appl. No. 13/248,704 Office Action dated Jun. 27, 2013.
U.S. Appl. No. 13/248,704 Office Action dated Mar. 17, 2016.
U.S. Appl. No. 13/248,704 Office Action dated Nov. 15, 2012.
U.S. Appl. No. 13/248,704 Office Action dated Sep. 22, 2015.
U.S. Appl. No. 13/248,704 Office Action dated Jan. 5, 2018.

* cited by examiner

OSTOMY POUCH FILTER SYSTEM

CROSS-REFERENCE

This application is a U.S. National Phase of PCT/US2015/027661, filed Apr. 24, 2015, which claims the benefit of U.S. Provisional Application No. 61/983,998, filed on Apr. 24, 2014, each of which is entirely incorporated herein by reference.

BACKGROUND OF THE INVENTION

An ostomy pouching system, or ostomy bag, is an ostomy appliance used to collect waste from a stoma created from a surgically diverted biological system. Such ostomy bags are commonly associated with colostomies, ileostomies, and urostomies. Gas produced during digestion can inflate and compromise an air-tight ostomy bag. Gas management and odor removal has been dealt with through the incorporation of a filter system within the ostomy bag, which vents this gas. It is desirable to design a filter system that is resistant to clogging by the accumulated waste within the pouch, thereby improving wear time of the ostomy bag.

SUMMARY OF THE INVENTION

In one aspect, disclosed herein are ostomy appliances comprising a front panel and a rear panel, at least partly sealed to one another along their peripheries, said front and rear panels forming a pouch, the rear panel having a stomal opening for positioning around a stoma so that body waste excreted through the stoma is captured in said pouch; a filter for deodorization of odorous gas from the body waste, said filter located on the front panel and said filter comprising an opening for emitting said deodorized gas to the atmosphere; and a center panel between the front and rear panels which at least partly covers said filter, the center panel having a bottom edge that is positioned above the bottom edges of the front and rear panels and is attached to the front and rear panels along the periphery of the pouch; wherein at least one of the center panel and front panel comprises one or more protrusions. In some embodiments, the center panel and front panel are partly attached to one another. In further embodiments, the center panel and front panel are attached by a single weld located on the center of the bottom edge of the center panel. In still further embodiments, the center panel and the front panel have a protrusion-free portion positioned between the filter and the single weld.

In some embodiments, the center panel comprises one or more protrusions that project toward the front panel. In some embodiments, the center panel comprises one or more protrusions that project toward the front panel and the front panel comprises one or more protrusions that project toward the center panel. In some embodiments, the front panel comprises one or more protrusions that project toward the center panel.

In another aspect, disclosed herein are ostomy appliances comprising a front panel and a rear panel, at least partly sealed to one another along their peripheries, said front and rear panels forming a pouch, the rear panel having a stomal opening for positioning around a stoma so that body waste excreted through the stoma is captured in said pouch; a filter for deodorization of odorous gas from the body waste, said filter located on the front panel and said filter comprising an opening for emitting said deodorized gas to the atmosphere; and a center panel between the front and rear panels which at least partly covers said filter, the center panel having a bottom edge that is positioned above the bottom edges of the front and rear panels and is attached to the front and rear panels along the periphery of the pouch, the center panel and front panel being attached by a single weld located on the center of the bottom edge of the center panel; wherein the center panel comprises one or more protrusions that project towards the front panel.

In another aspect, disclosed herein are ostomy appliances comprising a front panel and a rear panel, at least partly sealed to one another along their peripheries, said front and rear panels forming a pouch, the rear panel having a stomal opening for positioning around a stoma so that body waste excreted through the stoma is captured in said pouch; a filter for deodorization of odorous gas from the body waste, said filter located on the front panel and said filter comprising an opening for emitting said deodorized gas to the atmosphere; and a center panel between the front and rear panels which at least partly covers said filter, the center panel having a bottom edge that is positioned above the bottom edges of the front and rear panels and is attached to the front and rear panels along the periphery of the pouch, the center panel and front panel being attached by a single weld located on the center of the bottom edge of the center panel; wherein the center panel comprises one or more protrusions that project towards the front panel, and the center panel and the front panel have a substantially protrusion-free portion positioned between the filter and the single weld.

In some embodiments, the center panel comprises one or more protrusions which cover at least 50% of the surface area of the center panel. In some embodiments, the center panel comprises one or more protrusions which cover at least 66% of the surface area of the center panel. In some embodiments, the center panel comprises one or more protrusions which cover the entire surface area of the center panel.

In some embodiments, the one or more protrusions are half-spherical in shape. In some embodiments, the one or more protrusions are half-ovoidal in shape. In some embodiments, the one or more protrusions are polyhedral in shape. In further embodiments, the one or more protrusions are tetrahedral, pentahedral, or hexahedral in shape. In still further embodiments, the one or more protrusions have a top-face that is triangular, diamond-shaped, square-shaped, rectangular, pentagonal, hexagonal, heptagonal, or octagonal. In some embodiments, the one or more protrusions form a labyrinth pattern. In some embodiments, each of the one or more protrusions is one of at least two different shapes. In some embodiments, each of the one or more protrusions is one of at least two different sizes. In some embodiments, the one or more protrusions are arranged in columns. In some embodiments, the one or more protrusions are arranged in rows.

In some embodiments, the one or more protrusions are made of the same material as the center panel. In some embodiments, the one or more protrusions are integrally formed with the center panel.

In some embodiments, the filter is a round filter or a strip filter. In some embodiments, the filter is a radial flow filter or an axial flow filter.

In some embodiments, the pouch is drainable. In some embodiments, the pouch is closed.

In some embodiments, the center panel and front panel are attached by one or more additional welds located on the bottom edge of the center panel.

DETAILED DESCRIPTION OF THE INVENTION

Figure 1:
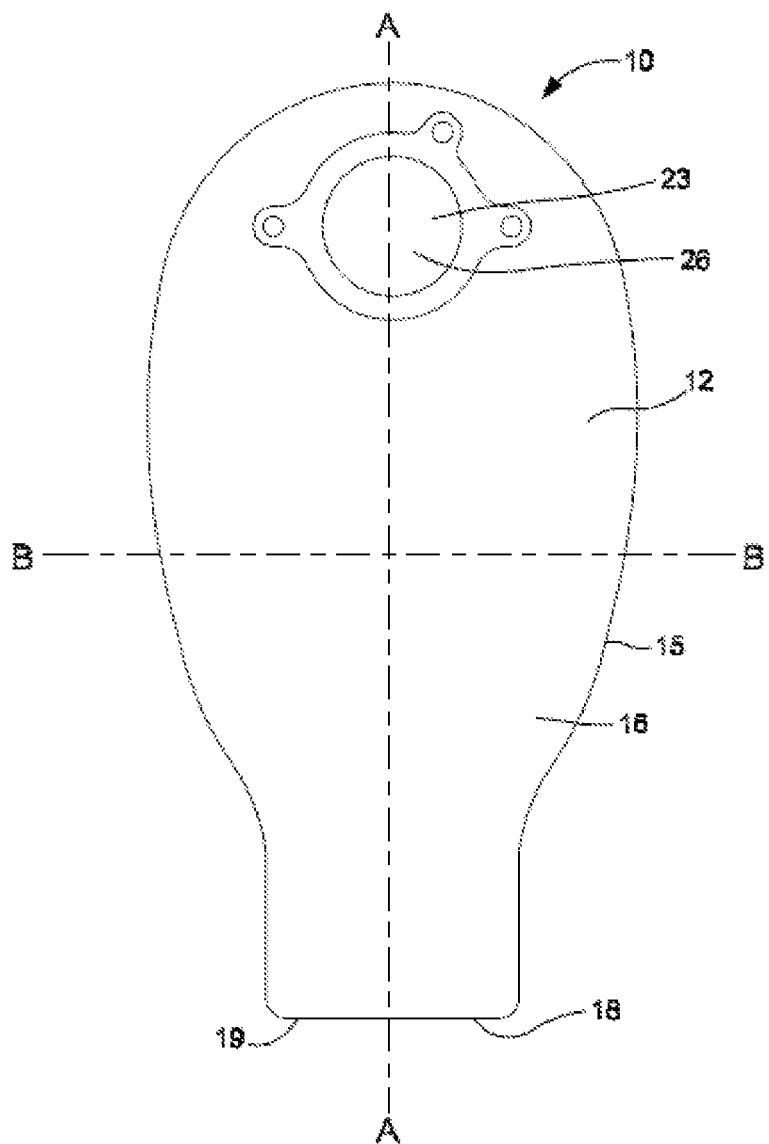
FIG. 1 is a rear elevational view of a first embodiment of an ostomy appliance in accordance with the present invention.

Ostomy pouch filters perform for a short time, usually a few hours and up to two days. These filters can fail by clogging which leads to ballooning, insufficient deodorization, or leakage, and results in overall reduced wear time of the pouch itself. The clogging may occur because the filter system becomes plugged or fouled with stool. As a result, the pouch no longer vents properly, causing ballooning of the pouch or continued flow of escaping gas without deodorization of odor. Additionally, there can be leakage of stool outside of the pouch from the filter vent opening.

Provided herein are ostomy pouch filter systems to be used in an ostomy appliance. The ostomy pouch filter systems described herein provide a method to resist clogging of the filter by waste within the ostomy pouch. The structure of the ostomy pouch filter systems described herein provide a tortuous path for waste that may enter the system, while allowing gas to pass freely to the filter.

Ostomy Appliance with Filter System

Disclosed herein, in certain embodiments, are ostomy appliances for the management of fecal or urinary waste. In some embodiments, the ostomy appliance comprises a front panel and a rear panel, at least partly sealed to one another along their peripheries, said front and rear panels forming a pouch, the rear panel having a stomal opening for positioning around a stoma so that body waste excreted through the stoma is captured in said pouch; a filter for deodorization of odorous gas from the body waste, said filter located on the front panel and said filter comprising an opening for emitting said deodorized gas to the atmosphere; and a center panel between the front and rear panels which at least partly covers said filter, the center panel having a bottom edge that is positioned above the bottom edges of the front and rear panels and is attached to the front and rear panels along the periphery of the pouch; wherein at least one of the center panel and front panel comprises one or more protrusions. In further embodiments, the center panel and front panel are partly attached to one another. In still further embodiments, the center panel and front panel are attached by a single weld located on the center of the bottom edge of the center panel. In still further embodiments, the center panel and the front panel have a protrusion-free portion positioned between the filter and the single weld. In still further embodiments, the center panel and the front panel have a substantially protrusion-free portion positioned between the filter and the single weld.

In some embodiments, the ostomy appliance comprises a front panel and a rear panel, at least partly sealed to one another along their peripheries, said front and rear panels forming a pouch, the rear panel having a stomal opening for positioning around a stoma so that body waste excreted through the stoma is captured in said pouch; a filter for deodorization of odorous gas from the body waste, said filter located on the front panel and said filter comprising an opening for emitting said deodorized gas to the atmosphere; and a center panel between the front and rear panels which at least partly covers said filter, the center panel having a bottom edge that is positioned above the bottom edges of the front and rear panels and is attached to the front and rear panels along the periphery of the pouch; wherein the center panel comprises one or more protrusions that project toward the front panel. In further embodiments, the center panel and front panel are partly attached to one another. In still further embodiments, the center panel and front panel are attached by a single weld located on the center of the bottom edge of the center panel. In still further embodiments, the center panel and the front panel have a protrusion-free portion positioned between the filter and the single weld. In still further embodiments, the center panel and the front panel have a substantially protrusion-free portion positioned between the filter and the single weld.

In some embodiments, the ostomy appliance comprises a front panel and a rear panel, at least partly sealed to one another along their peripheries, said front and rear panels forming a pouch, the rear panel having a stomal opening for positioning around a stoma so that body waste excreted through the stoma is captured in said pouch; a filter for deodorization of odorous gas from the body waste, said filter located on the front panel and said filter comprising an opening for emitting said deodorized gas to the atmosphere; and a center panel between the front and rear panels which at least partly covers said filter, the center panel having a bottom edge that is positioned above the bottom edges of the front and rear panels and is attached to the front and rear panels along the periphery of the pouch; wherein the front panel comprises one or more protrusions that project toward the center panel. In further embodiments, the center panel and front panel are partly attached to one another. In still further embodiments, the center panel and front panel are attached by a single weld located on the center of the bottom edge of the center panel. In still further embodiments, the center panel and the front panel have a protrusion-free portion positioned between the filter and the single weld. In still further embodiments, the center panel and the front panel have a substantially protrusion-free portion positioned between the filter and the single weld.

In some embodiments, the ostomy appliance comprises a front panel and a rear panel, at least partly sealed to one another along their peripheries, said front and rear panels forming a pouch, the rear panel having a stomal opening for positioning around a stoma so that body waste excreted through the stoma is captured in said pouch; a filter for deodorization of odorous gas from the body waste, said filter located on the front panel and said filter comprising an opening for emitting said deodorized gas to the atmosphere; and a center panel between the front and rear panels which at least partly covers said filter, the center panel having a bottom edge that is positioned above the bottom edges of the front and rear panels and is attached to the front and rear panels along the periphery of the pouch; wherein the center panel comprises one or more protrusions that project toward the front panel and the front panel comprises at least one protrusion that projects toward the center panel. In further embodiments, the center panel and front panel are partly attached to one another. In still further embodiments, the center panel and front panel are attached by a single weld located on the center of the bottom edge of the center panel. In still further embodiments, the center panel and the front panel have a protrusion-free portion positioned between the filter and the single weld. In still further embodiments, the center panel and the front panel have a substantially protrusion-free portion positioned between the filter and the single weld.

In some embodiments, the center panel comprises multiple protrusions which cover 20-50% of the surface area of the center panel. In some embodiments, the center panel comprises multiple protrusions which cover 30-60% of the surface area of the center panel. In some embodiments, the center panel comprises multiple protrusions which cover 40-70% of the surface area of the center panel. In some embodiments, the center panel comprises multiple protrusions which cover 50-80% of the surface area of the center panel. In some embodiments, the center panel comprises multiple protrusions which cover 75-90% of the surface area of the center panel. In some embodiments, the center panel comprises multiple protrusions which cover at least 50% of the surface area of the center panel. In some embodiments, the center panel comprises multiple protrusions which cover at least 66% of the surface area of the center panel. In some embodiments, the center panel comprises multiple protrusions which cover at least 80% of the surface area of the center panel. In some embodiments, the center panel comprises multiple protrusions which cover the entire surface area of the center panel.

In some embodiments, the front panel comprises multiple protrusions which cover 20-50% of the surface area of the front panel. In some embodiments, the front panel comprises multiple protrusions which cover 30-60% of the surface area of the front panel. In some embodiments, the front panel comprises multiple protrusions which cover 40-70% of the surface area of the front panel. In some embodiments, the front panel comprises multiple protrusions which cover 50-80% of the surface area of the front panel. In some embodiments, the front panel comprises multiple protrusions which cover 75-90% of the surface area of the front panel. In some embodiments, the front panel comprises multiple protrusions which cover at least 50% of the surface area of the front panel. In some embodiments, the front panel comprises multiple protrusions which cover at least 66% of the surface area of the front panel. In some embodiments, the front panel comprises multiple protrusions which cover at least 80% of the surface area of the front panel. In some embodiments, the front panel comprises multiple protrusions which cover the entire surface area of the front panel.

In some embodiments, each of the center panel and the front panel comprises multiple protrusions which cover 20-50% of the surface area of each of the center panel and the front panel. In some embodiments, each of the center panel and the front panel comprises multiple protrusions which cover 30-60% of the surface area of each of the center panel and the front panel. In some embodiments, each of the center panel and the front panel comprises multiple protrusions which cover 40-70% of the surface area of each of the center panel and the front panel. In some embodiments, each of the center panel and the front panel comprises multiple protrusions which cover 50-80% of the surface area of each of the center panel and the front panel. In some embodiments, each of the center panel and the front panel comprises multiple protrusions which cover 75-90% of the surface area of each of the center panel and the front panel. In some embodiments, each of the center panel and the front panel comprises multiple protrusions which cover at least 50% of the surface area of each of the center panel and the front panel. In some embodiments, each of the center panel and the front panel comprises multiple protrusions which cover at least 66% of the surface area of each of the center panel and the front panel. In some embodiments, each of the center panel and the front panel comprises multiple protrusions which cover at least 80% of the surface area of each of the center panel and the front panel. In some embodiments, each of the center panel and the front panel comprises multiple protrusions which cover the entire surface area of each of the center panel and the front panel.

In some embodiments discussed above and below, the substantially protrusion-free portion positioned between the filter and the single weld has less than 20% of the portion covered with protrusions. In some embodiments discussed above and below, the substantially protrusion-free portion positioned between the filter and the single weld has less than 15% of the portion covered with protrusions. In some embodiments discussed above and below, the substantially protrusion-free portion positioned between the filter and the single weld has less than 10% of the portion covered with protrusions. In some embodiments discussed above and below, the substantially protrusion-free portion positioned between the filter and the single weld has less than 5% of the portion covered with protrusions.

In some embodiments, the one or more protrusions are half-spherical in shape, half-ovoidal in shape, or polyhedral in shape, or a combination thereof in shape. In some embodiments, the one or more protrusions are half-spherical in shape. In some embodiments, the one or more protrusions are half-ovoidal in shape. In some embodiments, the one or more protrusions are polyhedral in shape. In some embodiments, the one or more protrusions are tetrahedral in shape. In some embodiments, the one or more protrusions are pentahedral in shape. In some embodiments, the one or more protrusions are hexahedral in shape. In some embodiments, the one or more protrusions have a polygonal top-face projected towards either the center panel or the front panel. In some embodiments, the one or more protrusions have a diamond-shaped top-face. In some embodiments, the one or more protrusions have a triangular top-face. In some embodiments, the one or more protrusions have a square-shaped top-face. In some embodiments, the one or more protrusions have a rectangular top-face. In some embodiments, the one or more protrusions have a pentagonal top-face. In some embodiments, the one or more protrusions have a hexagonal top-face. In some embodiments, the one or more protrusions have a heptagonal top-face. In some embodiments, the one or more protrusions have a octagonal top-face. In some embodiments, the one or more protrusions have a mixture of at least two shapes. In some embodiments, the one or more protrusions form a labyrinth pattern. In some embodiments, the one or more protrusions are a truncated half-sphere, truncated half-ovoid, or truncated polyhedron along the border of a protrusion-free portion of the center and front panels. In some embodiments, the one or more protrusions are uniform in size. In other embodiments, the one or more protrusions vary in size. In some embodiments, the one or more protrusions vary in size and in shape In some embodiments, the one or more protrusions are made of the same material as the center panel. In some embodiments, the one or more protrusions may be made of the same material as the center panel and shaped for example, by thermoforming. In some embodiments, the center panel is made of thermoplastic film. The thermoplastic film may be monolayer or coextruded type. In some embodiments, the one or more protrusions are integrally formed with the center panel. In some embodiments, the one or more protrusions are made of different material as the center panel and joined to the remainder of the center panel for form a unitary item. In some embodiments, the material of the protrusions has the same thickness as the material for the remainder of the center panel. In other embodiments, the material of the protrusions has a greater thickness than the material for the remainder of the center panel. In yet other embodiments, the material for the remainder of the center panel has a greater thickness than the material of the protrusions.

In some embodiments, the one or more protrusions are made of the same material as the front panel. In some embodiments, the one or more protrusions may be made of the same material as the front panel and shaped for example, by thermoforming. In some embodiments, the front panel is made of thermoplastic film. The thermoplastic film may be monolayer or coextruded type. In some embodiments, the one or more protrusions are integrally formed with the front panel. In some embodiments, the one or more protrusions are made of different material as the front panel and joined to the remainder of the front panel for form a unitary item. In some embodiments, the material of the protrusions has the same thickness as the material for the remainder of the front panel. In other embodiments, the material of the protrusions has a greater thickness than the material for the remainder of the front panel. In yet other embodiments, the material for the remainder of the front panel has a greater thickness than the material of the protrusions.

In some embodiments, at least 5% of the protrusions on the center panel are collapsed so as not to fully project towards the front panel. In some embodiments, at least 10% of the protrusions on the center panel are collapsed so as not to fully project towards the front panel. In some embodiments, at least 20% of the protrusions on the center panel are collapsed so as not to fully project towards the front panel. In some embodiments, at least 30% of the protrusions on the center panel are collapsed so as not to fully project towards the front panel. In some embodiments, at least 40% of the protrusions on the center panel are collapsed so as not to fully project towards the front panel. In some embodiments, at least 50% of the protrusions on the center panel are collapsed so as not to fully project towards the front panel. In some embodiments, at least 60% of the protrusions on the center panel are collapsed so as not to fully project towards the front panel. In some embodiments, at least 70% of the protrusions on the center panel are collapsed so as not to fully project towards the front panel. In some embodiments, at least 80% of the protrusions on the center panel are collapsed so as not to fully project towards the front panel. In some embodiments, at least 90% of the protrusions on the center panel are collapsed so as not to fully project towards the front panel. In some embodiments, less than 20% of the protrusions on the center panel are collapsed so as not to fully project towards the front panel. In some embodiments, less than 10% of the protrusions on the center panel are collapsed so as not to fully project towards the front panel.

In some embodiments, at least 5% of the protrusions on the front panel are collapsed so as not to fully project towards the center panel. In some embodiments, at least 10% of the protrusions on the front panel are collapsed so as not to fully project towards the center panel. In some embodiments, at least 20% of the protrusions on the front panel are collapsed so as not to fully project towards the center panel. In some embodiments, at least 30% of the protrusions on the front panel are collapsed so as not to fully project towards the center panel. In some embodiments, at least 40% of the protrusions on the front panel are collapsed so as not to fully project towards the center panel. In some embodiments, at least 50% of the protrusions on the front panel are collapsed so as not to fully project towards the center panel. In some embodiments, at least 60% of the protrusions on the front panel are collapsed so as not to fully project towards the center panel. In some embodiments, at least 70% of the protrusions on the front panel are collapsed so as not to fully project towards the center panel. In some embodiments, at least 80% of the protrusions on the front panel are collapsed so as not to fully project towards the center panel. In some embodiments, at least 90% of the protrusions on the front panel are collapsed so as not to fully project towards the center panel. In some embodiments, less than 20% of the protrusions on the front panel are collapsed so as not to fully project towards the center panel. In some embodiments, less than 10% of the protrusions on the front panel are collapsed so as not to fully project towards the center panel In some embodiments, the height of the protrusion is 0.5 mm to 5.0 mm. In some embodiments, the height of the protrusion is 1.0 mm to 5.0 mm. In some embodiments, the height of the protrusion is 0.5 mm to 4.0 mm. In some embodiments, the height of the protrusion is 2.0 mm to 4.0 mm. In some embodiments, the height of the protrusion is 0.5 mm to 3.5 mm. In some embodiments, the height of the protrusion is 1.0 mm to 3.5 mm. In some embodiments, the height of the protrusion is 1.5 mm to 3.5 mm. In some embodiments, the height of the protrusion is 0.5 mm to 3.0 mm. In some embodiments, the height of the protrusion is 1.0 mm to 3.0 mm. In some embodiments, the height of the protrusion is 1.6 mm to 3.0 mm. In some embodiments, the height of the protrusion is 1.7 mm to 3.0 mm. In some embodiments, the height of the protrusion is 1.8 mm to 3.0 mm. In some embodiments, the height of the protrusion is 1.9 mm to 3.0 mm. In some embodiments, the height of the protrusion is 2.0 mm to 3.0 mm.

In some embodiments, the average width of the protrusion is 0.5 mm to 10.0 mm. In some embodiments, the average width of the protrusion is 0.5 mm to 8.0 mm. In some embodiments, the average width of the protrusion is 0.5 mm to 5.0 mm. In some embodiments, the average width of the protrusion is 0.5 mm to 4.0 mm. In some embodiments, the average width of the protrusion is 0.5 mm to 3.0 mm. In some embodiments, the average width of the protrusion is 1.0 mm to 10.0 mm. In some embodiments, the average width of the protrusion is 1.0 mm to 8.0 mm. In some embodiments, the average width of the protrusion is 1.0 mm to 5.0 mm. In some embodiments, the average width of the protrusion is 1.0 mm to 4.0 mm. In some embodiments, the average width of the protrusion is 1.0 mm to 3.0 mm. In some embodiments, the average width of the protrusion is 2.0 mm to 10.0 mm. In some embodiments, the average width of the protrusion is 2.0 mm to 9.0 mm. In some embodiments, the average width of the protrusion is 2.0 mm to 8.0 mm. In some embodiments, the average width of the protrusion is 3.0 mm to 9 mm. In some embodiments, the average width of the protrusion is 3.0 mm to 8 mm. In some embodiments, the average width of the protrusion is 4.0 mm to 10.0 mm. In some embodiments, the average width of the protrusion is 4.0 mm to 9.0 mm. In some embodiments, the average width of the protrusion is 4.0 mm to 8.0 mm. In some embodiments, the average width of the protrusion is 1.0 mm. In some embodiments, the average width of the protrusion is 2.0 mm. In some embodiments, the average width of the protrusion is 3.0 mm. In some embodiments, the average width of the protrusion is 4.0 mm. In some embodiments, the average width of the protrusion is 5.0 mm. In some embodiments, the average width of the protrusion is 6.0 mm. In some embodiments, the average width of the protrusion is 7.0 mm. In some embodiments, the average width of the protrusion is 8.0 mm.

In some embodiments, the protrusions are arranged in columns. In further embodiments, adjacent columns are offset with respect to each other. In some embodiments, the protrusions are arranged in rows. In further embodiments, adjacent rows are offset with respect to each other.

In various embodiments, the spacing between protrusions is 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0 mm or more, including increments therein and combinations thereof. In some embodiments, the spacing between protrusions is 2.0 mm to 5.0 mm. In some embodiments, the spacing between protrusions is 2.0 mm to 10.0 mm. In some embodiments, the spacing between protrusions is 3.0 mm to 6.0 mm. In some embodiments, the spacing between protrusions is 3.0 mm to 10.0 mm. In some embodiments, the spacing between protrusions is 4.0 mm to 8.0 mm. In some embodiments, the spacing between protrusions is 4.0 mm to 10.0 mm. In some embodiments, the spacing between protrusions is 5.0 mm to 10.0 mm. In some embodiments, the spacing between protrusions is 3.0 mm to 4.0 mm.

The center panel may shield the filter from direct exposure to waste expelled from the stoma. In some embodiments, the bottom edge of the center panel is located below the horizontal pouch centerline. In other embodiments, the bottom edge of the center panel is located above the horizontal pouch centerline. In yet other embodiments, the bottom edge of the center panel is located along the horizontal pouch centerline. In further embodiments, the bottom edge of the center panel is below the stomal opening such that the center panel completely covers the stomal opening. In other embodiments, the center panel only partially covers the stomal opening. In some embodiments, the bottom edge of the center panel is below the stomal opening such that the center panel completely covers the stomal opening, the bottom edge of the center panel being located above the horizontal pouch centerline.

In some embodiments, the center panel and front panel are attached by a single weld located on the bottom edge of the center panel. In some embodiments, the single weld is shorter in length than the diameter of the stomal opening. In other embodiments, the single weld is longer in length than the diameter of the stomal opening. In still other embodiments, the single weld is the same length as the diameter of the stomal opening. In some embodiments, the single weld is shorter in length than the filter length or the diameter of the filter. In other embodiments, the single weld is longer in length than the filter length or the diameter of the filter. In still other embodiments, the single weld is the same length as the filter length or the diameter of the filter. In some embodiments, the single weld is longer than the filter length, or the diameter of the filter, but shorter than the diameter of the stomal opening. In other embodiments, the single weld is shorter in length than the filter length, or the diameter of the filter, and the diameter of the stomal opening. In yet other embodiments, the single weld is longer than the filter length, or the diameter of the filter, and the diameter of the stomal opening.

In some embodiments, the vertical single weld centerline is located along the vertical pouch centerline. In other embodiments, the vertical single weld centerline is offset from the vertical pouch centerline.

In some embodiments, the center panel and front panel are attached by two or more welds located on the bottom edge of the center panel. In some embodiments, two or more welds are positioned within 30 mm of the vertical pouch centerline. In some embodiments, two or more welds are positioned within 40 mm of the vertical pouch centerline. In some embodiments, two or more welds are positioned within 50 mm of the vertical pouch centerline. In some embodiments, a first weld is centrally located on the bottom edge of the center panel and one or more additional welds are located on the bottom edge of the center panel between the first weld and the periphery of the pouch. In further embodiments, the one or more additional welds are shorter in length than the first weld. In some embodiments, the first weld is about 10-50 mm in length and each of the one or more additional welds are about 2 to 10 mm in length. In some embodiments the first weld is 50 mm in length and each of the one or more additional welds are about 2 to 6 mm in length.

In some embodiments, the filter is a round filter or a strip filter. In some embodiments, the filter is a round filter. In some embodiments, the filter is a strip filter. In some embodiments, the filter is a radial flow filter or an axial flow filter. In some embodiments, the filter is a radial flow filter. In some embodiments, the filter is an axial flow filter.

In some embodiments, the filter is located above the stomal opening, with no overlap of the filter with the stomal opening. In other embodiments, the filter is located above the stomal opening, with partial overlap of the filter with the stomal opening. In still other embodiments, the filter and the stomal opening are positioned such that there is complete overlap between the filter and the stomal opening.

In some embodiments, the vertical filter centerline is located along the vertical pouch centerline. In some embodiments, the vertical filter centerline and the vertical stomal opening centerline are located along the vertical pouch centerline. In other embodiments, the vertical filter centerline is offset with respect to the vertical pouch centerline. In some embodiments, the vertical centerlines of the filter and the stomal opening are located along each other but are offset with respect to the vertical pouch centerline. In some embodiments, the vertical centerlines of the filter, the stomal opening, and the single weld are located along the vertical pouch centerline.

In some embodiments, the center panel and the front panel have a protrusion-free portion positioned between the filter and the single weld, such that the protrusion-free portion of the center panel that is exposed through the stomal opening is devoid of protrusions. In some embodiments, the center panel and the front panel have a protrusion-free portion positioned between the filter and the single weld, such that less than 50% of the surface area of the portion that is exposed through the stomal opening is covered by protrusions. In some embodiments, the center panel and the front panel have a protrusion-free portion positioned between the filter and the single weld, such that less than 40% of the surface area of the portion that is exposed through the stomal opening is covered by protrusions. In some embodiments, the center panel and the front panel have a protrusion-free portion positioned between the filter and the single weld, such that less than 30% of the surface area of the portion that is exposed through the stomal opening is covered by protrusions. In some embodiments, the center panel and the front panel have a protrusion-free portion positioned between the filter and the single weld, such that less than 20% of the surface area of the portion that is exposed through the stomal opening is covered by protrusions. In some embodiments, the center panel and the front panel have a protrusion-free portion positioned between the filter and the single weld, such that less than 10% of the surface area of the portion that is exposed through the stomal opening is covered by protrusions. In some embodiments, the center panel and the front panel have a protrusion-free portion positioned between the filter and the single weld, such that less than 5% of the surface area of the portion that is exposed through the stomal opening is covered by protrusions.

In some embodiments, the pouch is drainable. In some embodiments, the pouch is closed.

Figure 2:
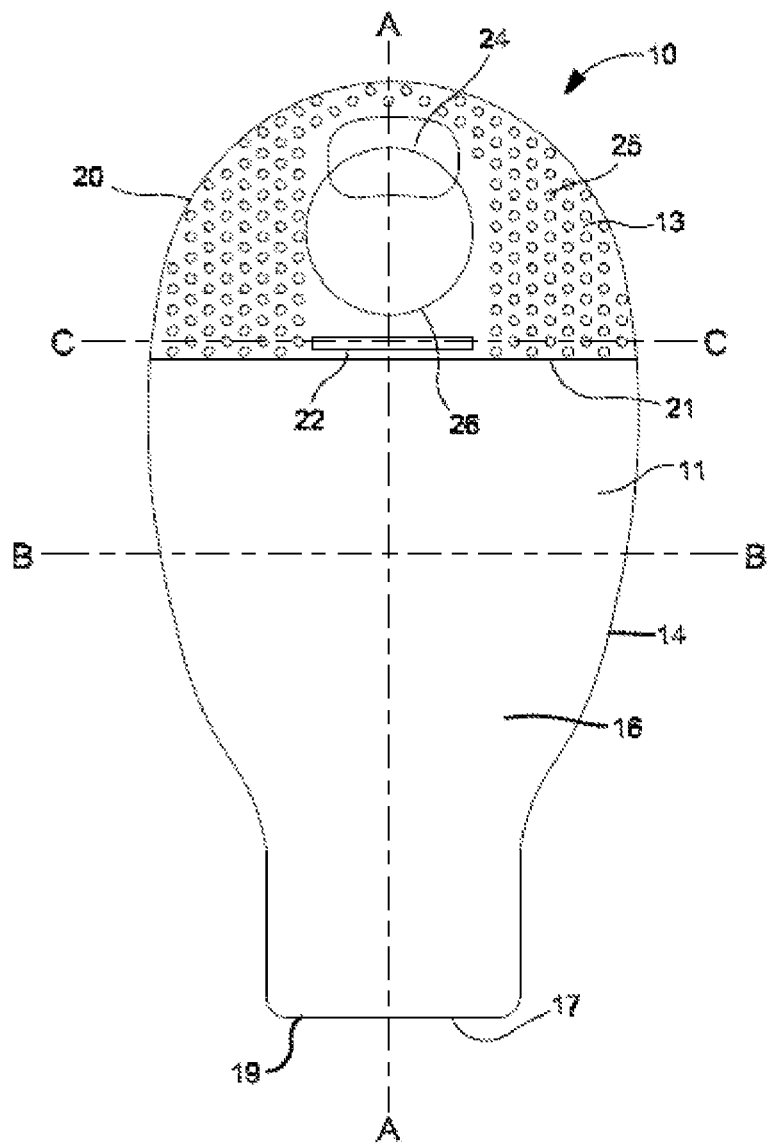
FIG. 2 is a front elevational view of the ostomy appliance of FIG. 1, without the stomal flange, for clarity.

Referring to FIGS. 1-2, an ostomy appliance 10 comprises a first embodiment of an ostomy pouch filter system. The ostomy appliance comprises a front panel 11, a rear panel 12, and a center panel 13. Front panel 11 and rear panel 12 are welded along their peripheries 14 and 15 except along their respective bottom edges 17 and 18 to form an ostomy pouch 16. The non-welded bottom edges 17 and 18 may include a drainage aperture 19 for drainage of the effluent collected in pouch. An alternative embodiment (not shown) has the front and rear panels completely welded along their peripheries, creating a closed pouch. As shown in FIG. 2, center panel 13 is viewed through the front panel 11. Center panel 13 is also welded to the front panel 11 and rear panel 12 along the respective peripheries 14, 15, and 20, except along the bottom edge 21 of the center panel. The bottom edge 21 of the center panel is positioned above the horizontal pouch centerline B-B. The center panel 13 and the front panel 11 are attached to one another by a single weld 22 located at the center of the bottom edge 21 of the center panel 13. The length of the single weld is shorter than the length of the filter. In alternative embodiments, the single weld is longer than the length of the filter.

The rear panel 12 has a stomal opening 23 for positioning around a stoma, the stomal opening 23 located above the horizontal pouch centerline B-B. The front panel 11 has a filter 24 located above the horizontal pouch centerline B-B, positioned higher than the stomal opening 23 but also partly overlapping the stomal opening 23. The vertical centerlines of the filter, the stomal opening, and the single weld are located along the vertical pouch centerline A-A.

The front, rear, and center panels 11, 12, and 13 may be made of flexible plastics film that is generally impermeable to liquid and gas. A suitable film includes, for example, a laminate of one or more layers of ethylene vinyl acetate (EVA), and one or more layers of a gas barrier material, such as poly(vinylidene chloride) (PVDC). At least one of the front and rear panels may further include one or more comfort layers lining the outer surface to provide a soft, comfortable outer surface. The films may be opaque. The films may be clear, or somewhat clear, so that the user may see through at least one of the front, center, and rear panels 11, 12, and 13.

The center panel 13 has multiple uniformly sized half-spherical protrusions 25 arranged in columns in which each adjacent column is offset with respect to each other. Each protrusion 25 projects towards the protrusion-free front panel 11, except if the protrusion 25 is collapsed. A collapsed protrusion is not able to fully project the top-face toward the front panel 11. The percentage of collapsed protrusions is adjusted by choice and thickness of material for the protrusions and/or method of protrusion preparation. A protrusion-free portion 26 on the center panel 13 is positioned between the single weld 22 and the filter 24, such that this portion 26 is in close contact with the front panel 11, minimizing effluent flow through this part of the filter system. The protrusion-free portion 26 of the center panel 13 that is exposed through the stomal opening 23 also presents a smooth surface to the stoma, reducing the potential for stomal irritation when in contact with the stoma.

Figure 3:
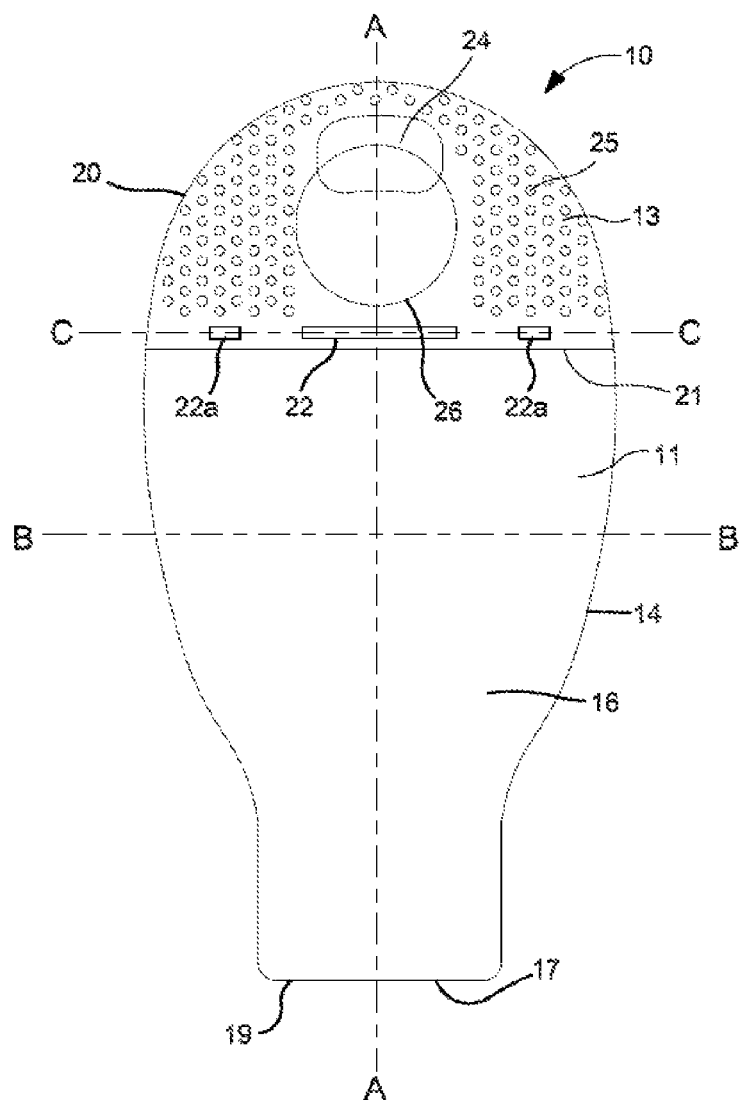
FIG. 3 is a front elevational view of a first alternative embodiment of FIG. 2, without the stomal flange, for clarity. This first alternative embodiment features two additional short welds, each of which is located between a centrally located long weld and the periphery of the ostomy appliance.

Referring to FIG. 3, an ostomy appliance comprises a first alternative embodiment of an ostomy appliance 10 wherein two additional welds 22a are located along the bottom edge 21 of the center panel 13 in addition to a weld 22. Weld 22 is centrally located and longer in length than either weld 22a. Each weld 22a is centrally located between weld 22 and periphery 14. In other embodiments (not shown), an ostomy appliance has one or more welds 22a anywhere along the bottom edge 21 of the center panel in addition to weld 22. In still other embodiments (not shown), the one or more welds 22a are located anywhere along bottom edge 21 between weld 22 and periphery 14. In some embodiments (not shown), the one or more welds 22a are shorter than weld 22. In some embodiments (not shown), the one or more welds 22a are the same length as weld 22. In some embodiments (not shown), the one or more welds 22a are longer than weld 22.

Figure 4:
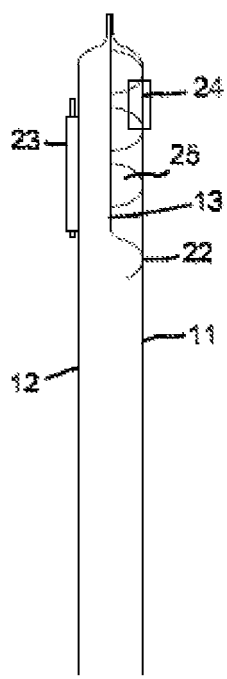
FIG. 4 is a cross-sectional view along line A-A of a second alternative embodiment of the ostomy appliance of FIG. 1. This second alternative embodiment features fewer and larger-sized half-spherical protrusions than those shown in the ostomy appliance of FIG. 1. The protrusions in this second alternative embodiment are not collapsed and fully project towards the front panel.
Figure 5:
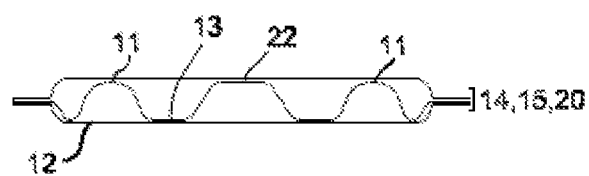
FIG. 5 is a cross-sectional view along line C-C of a second alternative embodiment of the ostomy appliance of FIG. 1. This second alternative embodiment is also shown in FIG. 3.

Referring to FIGS. 4-5, an ostomy appliance comprises a second alternative embodiment of an ostomy appliance 10 wherein the uniformly half-spherical protrusions 25 are larger in size. As shown in FIGS. 4-5, the protrusions 25 are not collapsed and fully project towards the front panel 11.

Figure 6:
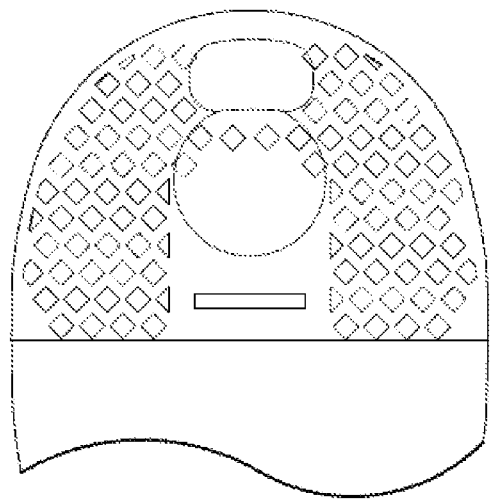
FIG. 6 is a front elevational view of a second embodiment of an ostomy appliance in accordance with the present invention.

Referring to FIG. 6, an ostomy appliance comprises a second embodiment of an ostomy pouch filter system comprising multiple uniformly sized protrusions with a polyhedral shape located only on the center panel. The diamond-shaped top-face of each protrusion projects toward the front panel, except if the protrusion is collapsed. A collapsed protrusion is not able to fully project the top-face toward the front panel. The protrusions are arranged in offset rows. At the border of the protrusion-free portion of the center panel between the single weld and the filter, the protrusions may have a truncated cubic shape.

Figure 7:
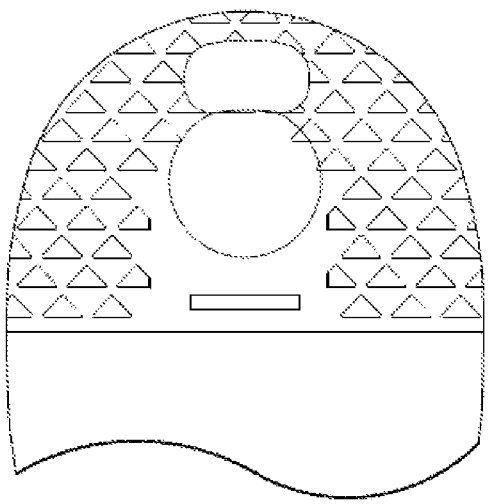
FIG. 7 is a front elevational view of a third embodiment of an ostomy appliance in accordance with the present invention.

Referring to FIG. 7, an ostomy appliance comprises a third embodiment of an ostomy pouch filter system comprising multiple uniformly sized protrusions with a polyhedral shape located only on the center panel. The triangular top-face of each protrusion projects toward the front panel, except if the protrusion is collapsed. A collapsed protrusion is not able to fully project the top-face toward the front panel. The protrusions are arranged in offset rows. At the border of the protrusion-free portion of the center panel between the single weld and the filter, the protrusions may have a truncated shape.

Figure 8:
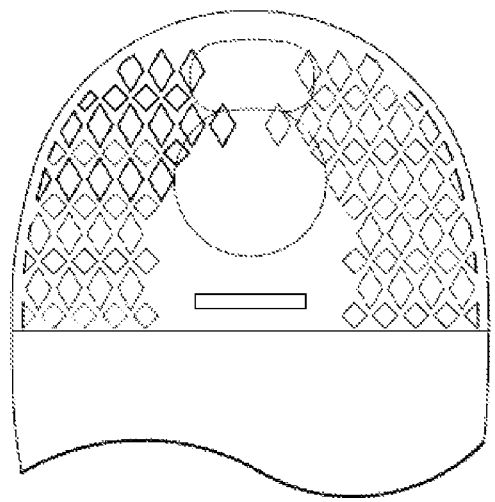
FIG. 8 is a front elevational view of a fourth embodiment of an ostomy appliance in accordance with the present invention.

Referring to FIG. 8, an ostomy appliance comprises a fourth embodiment of an ostomy pouch filter system comprising multiple protrusions with a polyhedral shape of two different sizes located only on the center panel. The diamond-shaped top-face of each protrusion projects toward the front panel, except if the protrusion is collapsed. A collapsed protrusion is not able to fully project the top-face toward the front panel. The protrusions are arranged in offset rows, with alternating rows of protrusions with large diamond-shaped top-faces and rows of protrusions with small diamond-shaped top-faces. At the border of the protrusion-free portion of the center panel between the single weld and the filter, the protrusions may have a truncated shape.

Figure 9:
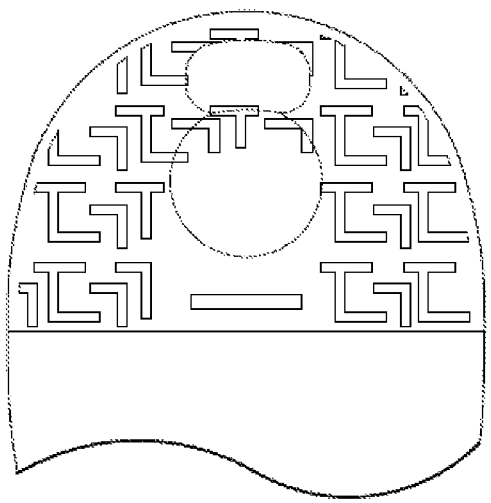
FIG. 9 is a front elevational view of a fifth embodiment of an ostomy appliance in accordance with the present invention.

Referring to FIG. 9, an ostomy appliance comprises a fifth embodiment of an ostomy pouch filter system comprising multiple protrusions located only on the center panel that create a labyrinth pattern. The top-face of each protrusion projects toward the front panel, except if the protrusion is collapsed. A collapsed protrusion is not able to fully project the top-face toward the front panel. At the border of the protrusion-free portion of the center panel between the single weld and the filter, the protrusions may have a truncated shape.

Other embodiments (not shown) of the ostomy appliance shown in FIGS. 4-9 have one or more additional welds 22a. The one or more additional welds are located along anywhere along bottom edge 21 between weld 22 and periphery 14. In some embodiments, the one or more welds 22a are shorter than weld 22. In some embodiments, the one or more welds 22a are the same length as weld 22. In some embodiments, the one or more welds 22a are longer than weld 22.

Figure 10:
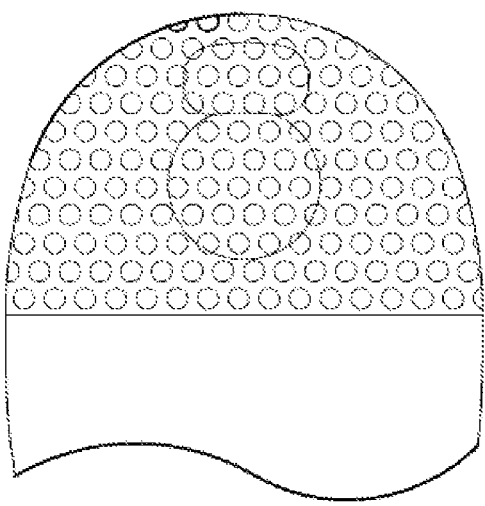
FIG. 10 is a front elevational view of a sixth embodiment of an ostomy appliance in accordance with the present invention.

Referring to FIG. 10, an ostomy appliance comprises a sixth embodiment of an ostomy pouch filter system comprising multiple uniformly sized protrusions with a half-spherical shape located only on the center panel. The top-face of each protrusion projects toward the front panel, except if the protrusion is collapsed. A collapsed protrusion is not able to fully project the top-face toward the front panel. The protrusions are arranged in offset columns. The protrusions are located on the entirely of the surface area of the center panel, with no protrusion-free portion between the single weld and the filter. There is no weld attaching the front and center panels. In other embodiments (not shown) of the sixth embodiment, the ostomy appliance has a single weld 22 attaching the front and center panels. In other embodiments (not shown) of the sixth embodiment, the ostomy appliance has a single weld 22 attaching the front and center panels and one or more welds 22a located along anywhere along bottom edge 21 between weld 22 and periphery 14. In some embodiments, the one or more welds 22a are shorter than weld 22. In some embodiments, the one or more welds 22a are the same length as weld 22. In some embodiments, the one or more welds 22a are longer than weld 22.

In order to mimic actual usage of ostomy pouches with filters and assess their resistance to clogging, tests were conducted on a specifically designed "tilting table" test rig. The test rig was designed to hold the test pouches in a vertical position and tilt to a horizontal position at timed intervals. The test rig also incorporated a means to inject air into the test pouches to simulate gas produced by the body. The test pouches were filled with a simulated stool referred to as Feclone, which was mixed to a desired viscosity to challenge the filtering system from a clogging perspective. During the tests, each test pouch was continuously cycled through the vertical and horizontal positions, and the filtering system of each test pouch was exposed to the simulated stool and simulated gas at timed intervals of 10 minutes at each position. During each cycle, the test pouches were injected with enough air to fill each pouch. The test pouch normally deflated by releasing the air through the filter system, unless the filter system failed. Testing was continued until all pouches had failed, as observed by pouch ballooning. When ballooning occurs, the simulated stool has clogged the filter, preventing the release of air through the filter. The criteria for filter system failure were the inability of the test pouch to deflate resulting in a fully ballooned pouch for three consecutive tilt table cycles.

Figure 11:
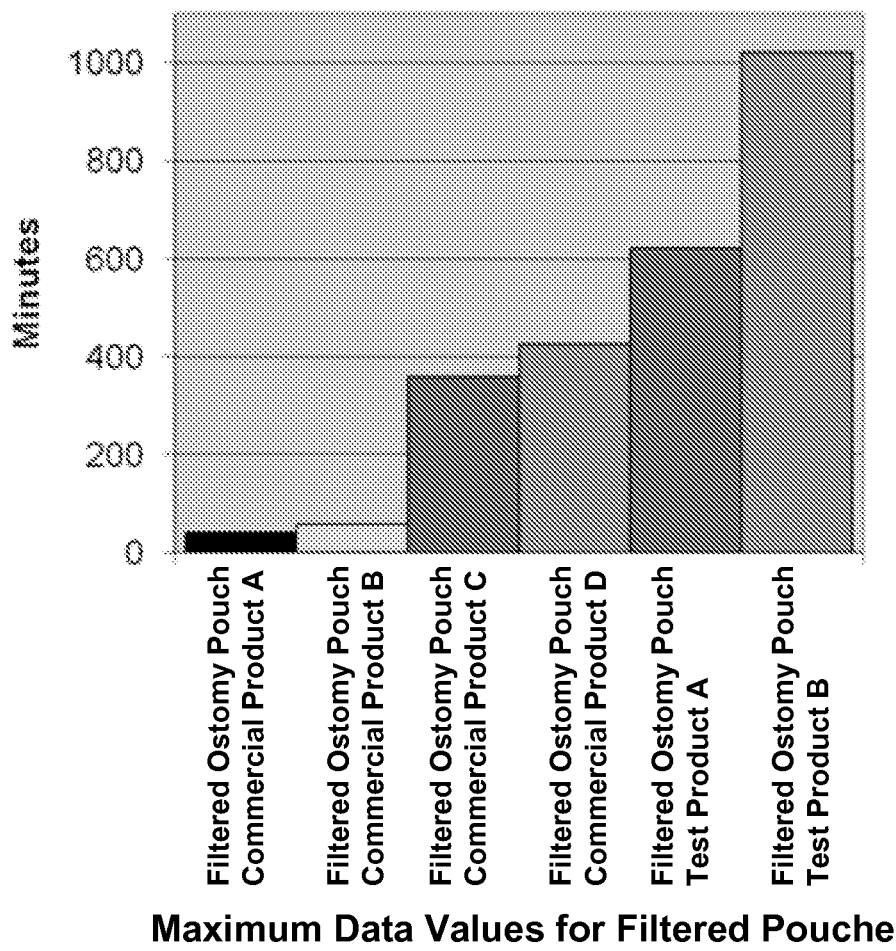
FIG. 11 is a graph of the filter life of various tested ostomy appliances as defined by time to clog and as tested by tilt table.

Numerous commercial filtering systems were evaluated. Test results of various pouch designs, with different filtering systems, are summarized in FIG. 11. Filter system A ("Test Product A") is one embodiment of the present invention and is illustrated in FIG. 10. Filter system B ("Test Product B") is another embodiment of the present invention and is illustrated in FIGS. 1-2. The test results indicated that Filter system A had a 33% longer filter life than a filter system with a pleated center panel incorporated in a commercially available ostomy pouch (Convatec Esteem Plus). Filter system B had a 150% longer filter life than a filter system with a pleated center panel incorporated in a commercially available ostomy pouch ("Commercial Product D"; Convatec Esteem Plus).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An ostomy appliance comprising
   a. a front panel and a rear panel, at least partly sealed to one another along their peripheries, said front and rear panels forming a pouch, the rear panel having a stomal opening for positioning around a stoma so that body waste excreted through the stoma is captured in said pouch;
   b. a filter for deodorization of odorous gas from the body waste, said filter located on the front panel and said filter comprising an opening for emitting said deodorized gas to the atmosphere; and
   c. a center panel between the front and rear panels which at least partly covers said filter, the center panel having a bottom edge that is positioned above the bottom edges of the front and rear panels and is attached to the front and rear panels along the periphery of the pouch;
   wherein the center panel comprises an area comprising one or more protrusions and an area that is substantially protrusion-free, wherein a portion of the center panel is exposed through the stomal opening, and wherein the portion of the center panel exposed through the stomal opening is within the area that is substantially protrusion-free.

2. The ostomy appliance of claim 1, wherein the center panel and front panel are partly attached to one another.

3. The ostomy appliance of claim 1, wherein the center panel and front panel are attached by a single weld located on the center of the bottom edge of the center panel.

4. The ostomy appliance of claim 3, wherein the area that is substantially protrusion-free is positioned between the filter and the single weld.

5. The ostomy appliance of claim 1, wherein the one or more protrusions project toward the front panel.

6. The ostomy appliance of claim 1, wherein the center panel comprises one or more protrusions that project toward the front panel and the front panel comprises one or more protrusions that project toward the center panel.

7. An ostomy appliance comprising
   a. a front panel and a rear panel, at least partly sealed to one another along their peripheries, said front and rear panels forming a pouch, the rear panel having a stomal opening for positioning around a stoma so that body waste excreted through the stoma is captured in said pouch;
   b. a filter for deodorization of odorous gas from the body waste, said filter located on the front panel and said filter comprising an opening for emitting said deodorized gas to the atmosphere; and
   c. a center panel between the front and rear panels which at least partly covers said filter, the center panel having a bottom edge that is positioned above the bottom edges of the front and rear panels and is attached to the front and rear panels along the periphery of the pouch, the center panel and front panel being attached by a single weld located on the center of the bottom edge of the center panel, wherein the single weld is shorter than the bottom edge of the center panel;
wherein the center panel comprises one or more protrusions that project towards the front panel.

8. An ostomy appliance comprising
   a. a front panel and a rear panel, at least partly sealed to one another along their peripheries, said front and rear panels forming a pouch, the rear panel having a stomal opening for positioning around a stoma so that body waste excreted through the stoma is captured in said pouch;
   b. a filter for deodorization of odorous gas from the body waste, said filter located on the front panel and said filter comprising an opening for emitting said deodorized gas to the atmosphere; and
   c. a center panel between the front and rear panels which at least partly covers said filter, the center panel having a bottom edge that is positioned above the bottom edges of the front and rear panels and is attached to the front and rear panels along the periphery of the pouch, the center panel and front panel being attached by a single weld located on the center of the bottom edge of the center panel;
wherein the center panel comprises an area comprising one or more protrusions that project towards the front panel, and an area that is substantially protrusion-free, wherein the area that is substantially protrusion-free portion is positioned between the filter and the single weld.

9. The ostomy appliance of claim 1, wherein the center panel comprises one or more protrusions which cover at least 50% of the surface area of the center panel.

10. The ostomy appliance of claim 1, wherein the center panel comprises one or more protrusions which cover at least 66% of the surface area of the center panel.

11. The ostomy appliance of claim 1, wherein the center panel comprises one or more protrusions which cover the entire surface area of the center panel.

12. The ostomy appliance of claim 1, wherein the front panel comprises one or more protrusions that project toward the center panel.

13. The ostomy appliance of claim 1, wherein the one or more protrusions are half-spherical in shape.

14. The ostomy appliance of claim 1, wherein the one or more protrusions are half-ovoidal in shape.

15. The ostomy appliance of claim 1, wherein the one or more protrusions are polyhedral in shape.

16. The ostomy appliance of claim 1, wherein the one or more protrusions form a labyrinth pattern.

17. The ostomy appliance of claim 15, wherein the one or more protrusions are tetrahedral, pentahedral, or hexahedral in shape.

18. The ostomy appliance of claim 17, wherein the one or more protrusions have a top-face that is triangular, diamond-shaped, square-shaped, rectangular, pentagonal, hexagonal, heptagonal, or octagonal.

19. The ostomy appliance of claim 1, wherein each of the one or more protrusions is one of at least two different shapes.

20. The ostomy appliance claim 1, wherein each of the one or more protrusions is one of at least two different sizes.

21. The ostomy appliance of claim 1, wherein the one or more protrusions are arranged in columns.

22. The ostomy appliance of claim 1, wherein the one or more protrusions are arranged in rows.

23. The ostomy appliance of claim 1, wherein the filter is a round filter or a strip filter.

24. The ostomy appliance of claim 1, wherein the filter is a radial flow filter or an axial flow filter.

25. The ostomy appliance of claim 1, wherein the one or more protrusions are made of the same material as the center panel.

26. The ostomy appliance of claim 1, wherein the one or more protrusions are integrally formed with the center panel.

27. The ostomy appliance of claim 1, wherein the pouch is drainable.

28. The ostomy appliance of claim 1, wherein the pouch is closed.

29. The ostomy appliance of claim 1, wherein the center panel and front panel are attached by one or more additional welds located on the bottom edge of the center panel.

* * * * *